(12) United States Patent
Tezuka

(10) Patent No.: US 11,079,341 B2
(45) Date of Patent: Aug. 3, 2021

(54) RADIATION IMAGING APPARATUS, CONTROL APPARATUS, AND CONTROL METHODS AND STORAGE MEDIUMS THEREFOR

(71) Applicant: CANON KABUSHIKI KAISHA, Tokyo (JP)

(72) Inventor: Shimpei Tezuka, Oyama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 44 days.

(21) Appl. No.: 16/580,269

(22) Filed: Sep. 24, 2019

(65) Prior Publication Data

US 2020/0018710 A1 Jan. 16, 2020

Related U.S. Application Data

(63) Continuation of application No. PCT/JP2018/006692, filed on Feb. 23, 2018.

(30) Foreign Application Priority Data

Apr. 28, 2017 (JP) .............................. JP2017-090235

(51) Int. Cl.
*G01N 23/02* (2006.01)
*G01T 1/208* (2006.01)
*G01T 1/24* (2006.01)

(52) U.S. Cl.
CPC .............. *G01N 23/02* (2013.01); *G01T 1/208* (2013.01); *G01T 1/247* (2013.01)

(58) Field of Classification Search
CPC .......... G01N 23/02; G01T 1/208; G01T 1/247
See application file for complete search history.

(56) References Cited

U.S. PATENT DOCUMENTS

| | | | |
|---|---|---|---|
| 7,677,800 B2 | 3/2010 | Agano et al. | |
| 9,395,450 B2 | 7/2016 | Tezuka | |
| 10,498,975 B2 | 12/2019 | Tezuka et al. | |
| 2008/0284857 A1* | 11/2008 | Yoshida | H04N 5/23206 348/207.99 |
| 2013/0336445 A1* | 12/2013 | Sehnert | A61B 6/487 378/42 |
| 2016/0350923 A1* | 12/2016 | Muraoka | G06T 5/008 |

FOREIGN PATENT DOCUMENTS

| | | |
|---|---|---|
| JP | 2002-032295 | 1/2002 |
| JP | 2002-330429 | 11/2002 |
| JP | 2008-237230 | 10/2008 |
| JP | 2013-226243 | 11/2013 |
| JP | 2014-068183 | 4/2014 |

* cited by examiner

*Primary Examiner* — Hugh Maupin
(74) *Attorney, Agent, or Firm* — Venable LLP

(57) ABSTRACT

A radiation imaging apparatus comprising: an imaging unit configured to capture a radiation image; a generation unit configured to generate each of thinned images of a plurality of radiation images captured by the imaging unit; and a transfer unit configured to wirelessly transfer a plurality of thinned images, wherein the transfer unit transfers each of remaining untransferred images obtained by excluding the thinned images from the radiation images after completion of the transfer of the plurality of thinned images.

24 Claims, 13 Drawing Sheets

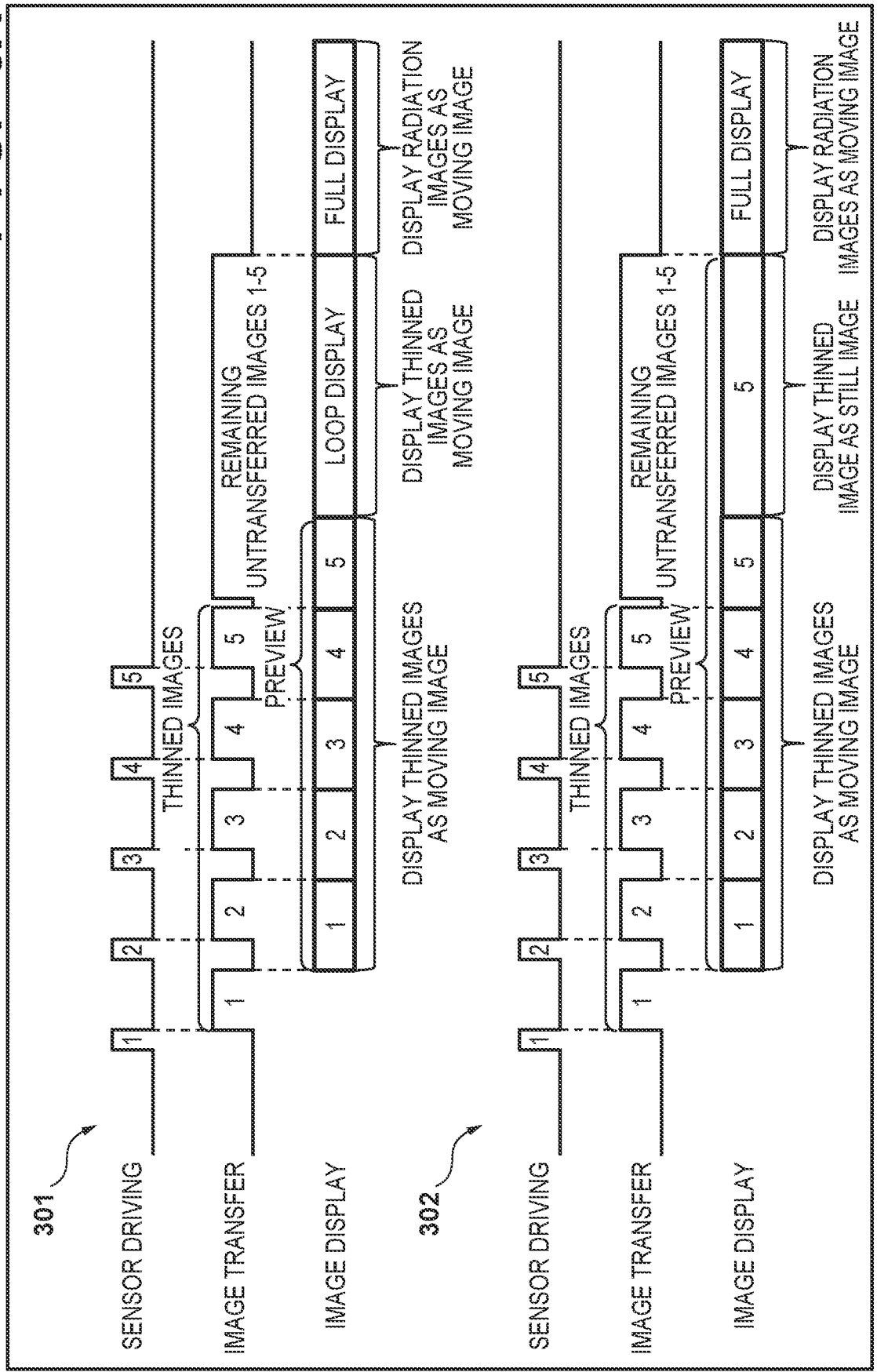

| IMAGING MODE No. | SIZE [cm] | BINNING | FRAME RATE [fps] | OUTPUT GAIN |
|---|---|---|---|---|
| 1 | 43x43 | 3x3 | 30 | 20 |
| 2 | 43x43 | 2x2 | 15 | 3 |
| 3 | 43x43 | 1x1 | 1 | 1 |
| 4 | 30x30 | 2x2 | 30 | 10 |
| 5 | 15x15 | 1x1 | 15 | 5 |
| ... | ... | ... | ... | ... |

| IMAGING TECHNIQUE | IMAGING MODE NO. | IMAGING NUMBER | PREVIEW TRANSFER EXECUTION FRAME NUMBER |
|---|---|---|---|
| A | 2 | 70 | 0,15,30,45,60 |
| B | 5 | 3 | 0 |
| C | 1 | 100 | 0,20,50,99 |
| ... | ... | ... | ... |

RADIATION IMAGING APPARATUS, CONTROL APPARATUS, AND CONTROL METHODS AND STORAGE MEDIUMS THEREFOR

CROSS-REFERENCE TO RELATED APPLICATIONS

This application is a Continuation of International Patent Application No. PCT/JP2018/006692, filed Feb. 23, 2018, which claims the benefit of Japanese Patent Application No. 2017-090235, filed Apr. 28, 2017, both of which are hereby incorporated by reference herein in their entirety.

BACKGROUND OF THE INVENTION

Field of the Invention

The present invention relates to a radiation imaging apparatus, a control apparatus, and control methods and storage mediums therefor.

Background Art

Conventionally, a radiation imaging apparatus, and a radiation imaging system in which a sharp radiation image is obtained by irradiating an object with radiation from a radiation generation apparatus, converting the intensity distribution of radiation transmitted through the object into digital data, and performing image processing for the digital radiation image are commercially available.

In such radiation image capturing system, the radiation generation apparatus performs radiation irradiation, and radiation image data obtained by the radiation imaging apparatus is transferred to a control apparatus such as a control computer for medical image diagnosis and storage.

For the radiation imaging apparatus, a sensor array in which pixels each formed by a conversion element that converts radiation into signal charges (an electrical signal) and a switch element such as a TFT (Thin Film Transistor) that externally transfers the electrical signal are arrayed two-dimensionally is used. The signal charges converted by the conversion element using the switch element such as a TFT are read out, and a digital image is formed from the amount of the readout charges.

In recent years, a portable radiation imaging apparatus that requires no cable connection by transferring a formed digital image to a control apparatus by wireless communication and including a rechargeable battery in the radiation imaging apparatus has been put into practice.

PTL 1 discloses a method of continuously transmitting, to a control apparatus, only preview images whose image sizes are reduced from images of a plurality of frames continuously captured, and displaying them.

CITATION LIST

Patent Literature

PTL 1: Japanese Patent Laid Open No. 2013-226243

However, the technique described in PTL 1 does not disclose a technique of transferring remaining untransferred images after completion of transfer of a plurality of thinned images corresponding to preview images.

The present invention has been made in consideration of the above problem, and provides a technique for displaying a plurality of thinned images as a moving image and displaying, as a moving image, a plurality of radiation images whose image sizes are not reduced.

SUMMARY OF THE INVENTION

To achieve the above object, there is provided a radiation imaging apparatus comprising:
an imaging unit configured to capture a radiation image;
a generation unit configured to generate each of thinned images of a plurality of radiation images captured by the imaging unit; and
a transfer unit configured to wirelessly transfer a plurality of thinned images,
wherein the transfer unit transfers each of remaining untransferred images obtained by excluding the thinned images from the radiation images after completion of the transfer of the plurality of thinned images.

Further features of the present invention will become apparent from the following description of exemplary embodiments with reference to the attached drawings.

BRIEF DESCRIPTION OF THE DRAWINGS

The accompanying drawings, which are incorporated in and constitute a part of the specification, illustrate embodiments of the invention and, together with the description, serve to explain the principles of the invention.

FIG. 3A is a timing chart showing an example of the imaging operation of the radiation imaging system according to the first embodiment;

DESCRIPTION OF THE EMBODIMENTS

Embodiments will be described below with reference to the accompanying drawings. Note that arrangements described in the following embodiments are merely examples, and details of sizes and structures shown in the respective embodiments are not limited to the specification and drawings. Note also that in this specification, radiation includes not only X-rays but also α-rays, β-rays, γ-rays, and various kinds of particle beams.

First Embodiment

In this embodiment, if it is possible to transfer thinned image data in real time, an moving image of thinned image data is displayed (preview-displayed) at a transfer destination, and untransferred image data (that is, the difference between original image data and the thinned image data) are transferred after transfer of the thinned image data. After that, the original image data are displayed/stored in the transfer destination. On the other hand, if it is impossible to transfer thinned image data in real time, transfer is executed by changing a transfer frame rate in accordance with a communication status or changing the size of each thinned image data.

<System Arrangement>

Figure 1:
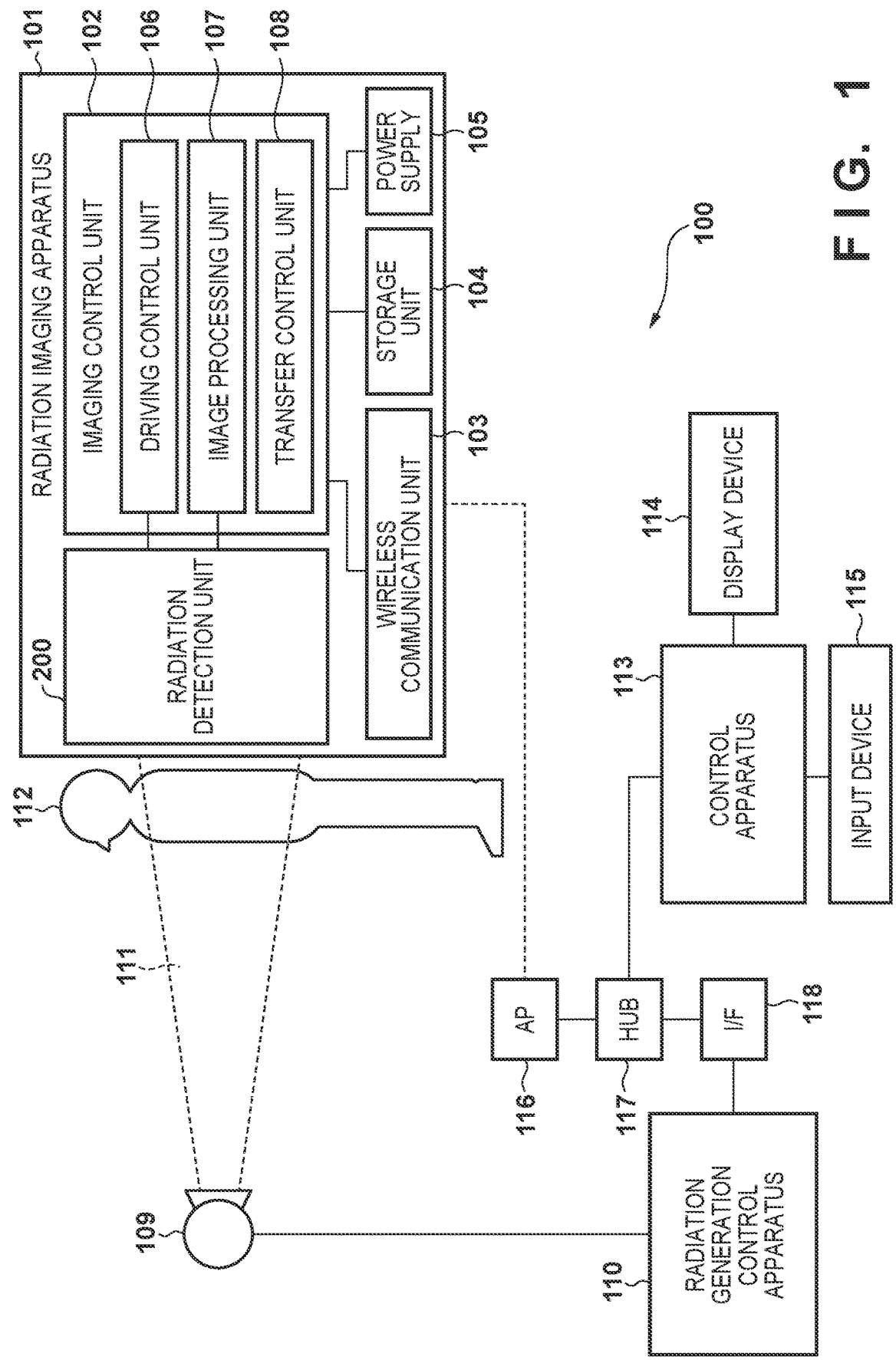
FIG. 1 is a view showing an example of the arrangement of a radiation imaging system.

FIG. 1 is a view showing an example of the schematic arrangement of a radiation imaging system 100 according to the first embodiment of the present invention. The radiation imaging system 100 includes a radiation imaging apparatus 101, a radiation source 109, a radiation generation control apparatus 110, a control apparatus 113, a display device 114, an input device 115, an access point 116, a HUB 117, and an interface unit I/F 118. However, not all the components shown in FIG. 1 need to be included. For example, the radiation imaging system 100 need only be formed by including at least the radiation imaging apparatus 101 and the control apparatus 113.

The radiation imaging apparatus 101 is an apparatus that obtains radiation image data of an object 112 based on radiation 111 emitted from the radiation source 109 and transmitted through the object 112, and is, for example, an apparatus using a flat panel detector (FPD). The radiation imaging apparatus 101 includes a radiation detection unit 200, an imaging control unit 102, a wireless communication unit 103, a storage unit 104, and a power supply 105. However, not all the components need be included. For example, the radiation imaging apparatus 101 need only be formed by including at least the radiation detection unit 200 and the imaging control unit 102.

The radiation detection unit 200 detects radiation, and generates captured image data in accordance with the detected radiation. The radiation detection unit 200 can obtain a plurality of radiation images as a moving image by performing imaging a plurality of times.

The imaging control unit 102 includes a driving control unit 106, an image processing unit 107, and a transfer control unit 108. The imaging control unit 102 performs processes associated with driving control of the radiation detection unit 200, various image processes for captured image data, storage of image data, determination of a transfer timing, transfer control, and the like. The image data processed by the imaging control unit 102 are transferred to the control apparatus 113 and the like.

The driving control unit 106 controls driving of the radiation detection unit 200, a readout operation, and the like. The image processing unit 107 performs various processes for obtained digital image information. The image processing unit 107 performs, for example, correction processing for correcting a defect or offset of an image, image processing including processing for reducing various kinds of noise, and the like. Furthermore, thinned image generation processing of, for example, generating thinned image data by performing thinning processing for a preview by thinning out only some pixels from a captured image is included. Note that the image processing unit need not perform all the processes necessary to generate an image to be transferred to the control apparatus, and need only perform necessary processes. The remaining processes can be executed in, for example, the external control apparatus.

The transfer control unit 108 controls transfer of captured images having undergone image processing. There is not only a case in which overall images are transferred but also a case in which thinned images each generated from part of pixel information of a captured image are transferred. If partial pixel data obtained by performing thinning processing are transferred first as thinned images, images corresponding to the remaining pixel data not used for a preview may be transferred as untransferred images.

The storage unit 104 is a device such as a flash memory, and stores image data processed by the image processing unit 107 and various kinds of information accompanying the image data. The various kinds of information accompanying the image data include information concerning a captured patient, information concerning a radiographer, information concerning a captured portion, information concerning the imaging date/time, and, for a moving image, information such as a unique ID for identifying an obtained frame. The storage unit 104 can store one or some of these pieces of information in association with the image data. Transfer execution information indicating whether the transfer control unit 108 has transferred the images in real time can also be stored in association with the image data. Furthermore, the storage unit 104 can store defect information, gain information, offset information, and the like to be used for image correction, and can also be used to store the operation log of the radiation imaging apparatus 101.

The wireless communication unit 103 includes, for example, an antenna, and wirelessly transmits the image data stored in the storage unit 104 and the like to the external control apparatus 113 and the like under the control of the transfer control unit 108. Furthermore, information transmitted/received by the wireless communication unit 103 may include other information (for example, synchronization information for radiation imaging) in addition to the radiation image data. For example, the information may include operation mode setting information from the control apparatus 113, command communication information for confirmation of the state of the radiation imaging apparatus 101, and signal information of an imaging start request and a stop request by an imaging switch from the radiation generation control apparatus 110. The information may also include notification information of a radiation irradiation enable period from the radiation imaging apparatus 101.

The power supply 105 is a power supply unit for the operation of the radiation imaging apparatus 101. The power supply 105 may be formed as a battery detachable from the radiation imaging apparatus 101 or as a capacitor or a battery rechargeable by receiving power supply from the outside.

The control apparatus 113 performs, by a control unit such as a CPU (not shown), various control operations such as control of the operation, imaging mode, and the like of the radiation imaging system 100 and processing of image data captured by the radiation imaging apparatus 101. One of various computers and workstations can be used as the control apparatus 113. The control apparatus 113 may be connected to the display device 114 such as a display for displaying a menu for control, image data after imaging, and the like, and the input device 115 such as a mouse and a keyboard for performing various input operations, and may control the operations of these devices.

The radiation source 109 is formed by an electron gun for generating the radiation 111, a rotor, and the like. The radiation generation control apparatus 110 controls the operation of the radiation source 109. Electrons collide with the rotor while being accelerated by the high voltage generated by the radiation generation control apparatus 110, thereby generating radiation. In addition, the radiation generation control apparatus 110 may be connected to a switch (not shown) for requesting radiation imaging, such as an irradiation switch or a fluoroscopy pedal, and an operation unit (not shown) for setting radiation irradiation conditions Communication between the radiation imaging apparatus 101 and the control apparatus 113 is performed by a wireless LAN via the access point 116. However, when one of the radiation imaging apparatus 101 and the control apparatus 113 may serve as an access point to perform direct communication without intervention of the access point 116. Alternatively, another wireless communication method such as Bluetooth® may be used.

The interface unit 118 is provided between the control apparatus 113 and the radiation generation control apparatus 110. The interface unit 118 includes a circuit that mediates communication performed between the radiation imaging apparatus 101 and the radiation generation control apparatus 110, and relays exchange of a synchronization signal and the like. The interface unit 118 can adjust the irradiation timing of radiation from the radiation source 109 in accordance with, for example, the state of the radiation imaging apparatus 101 by monitoring the states of the radiation imaging apparatus 101 and the radiation generation control apparatus 110. Furthermore, when the interface unit 118 is connected to the control apparatus 113, it can relay various control signals and information.

The interface unit 118 is connected to the control apparatus 113 by Ethernet via the HUB 117. The HUB 117 is a unit for connecting a plurality of network apparatuses. Furthermore, the interface unit 118 is also connected to the radiation imaging apparatus 101 by a wireless LAN by connecting the access point 116 to the HUB 117.

<Arrangement of Radiation Detection Unit>

Figure 2:
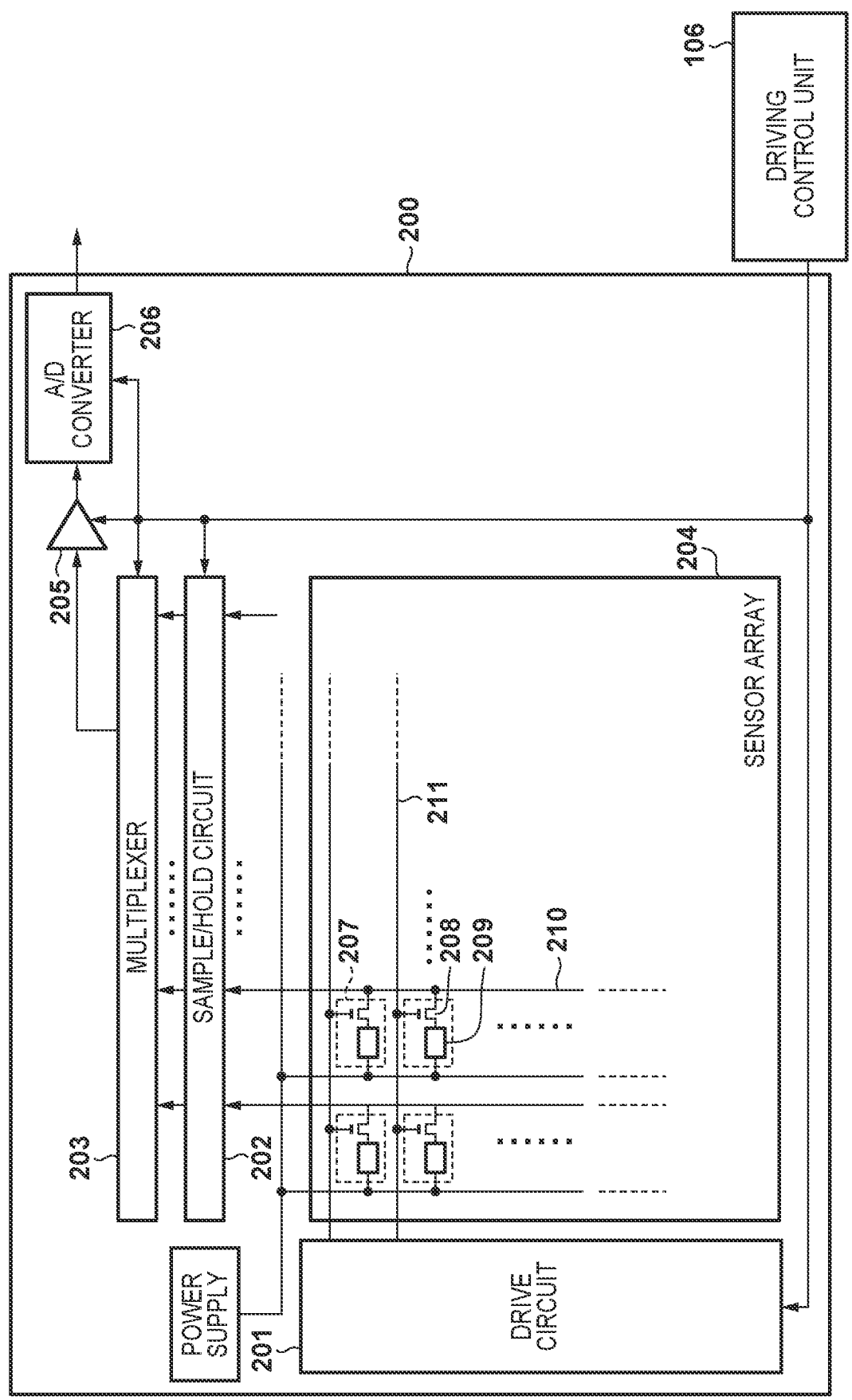
FIG. 2 is a circuit diagram showing the schematic arrangement of a radiation detection unit in a radiation imaging apparatus.

FIG. 2 shows an example of the arrangement of the radiation detection unit 200. The radiation detection unit 200 can operate under the control of the driving control unit 106, and includes a drive circuit 201, a sample/hold circuit 202, a multiplexer 203, a sensor array 204, an amplifier 205, and an A/D converter 206.

The sensor array 204 includes a plurality of pixels arranged in a two-dimensional array to form a plurality of rows and a plurality of columns. Each pixel 207 on the sensor array 204 includes, for example, a switch element 208 such as a TFT and a photoelectric conversion element 209, and is formed by providing, for example, a phosphor thereon. In this case, radiation entering the radiation detection unit 200 is converted into visible light through the phosphor, and the converted visible light enters the photoelectric conversion element 209 of each pixel 207, thereby generating charges corresponding to the visible light in each photoelectric conversion element 209. Note that in this embodiment, the above-described phosphor and photoelectric conversion element form a conversion element that converts incident radiation into charges. For example, a so-called direct conversion type conversion element that directly converts incident radiation into charges may be formed without providing any phosphor. It is possible to accumulate charges and read out the charges by switching ON/OFF of the TFTs 208, thereby obtaining a radiation image.

In each pixel on a given row on the two-dimensional sensor array 204 of the radiation detection unit 200, if the drive circuit 201 applies the ON voltage of the TFT to a driving line 211, the TFT of each pixel on the row is turned on. Then, charges are held in the sample/hold circuit 202 through a corresponding signal line 210. After that, the held charges output from the pixels are sequentially read out via the multiplexer 203, amplified by the amplifier 205, and then converted into digital image data by the A/D converter 206. With respect to a row for which a charge readout operation has ended, when the drive circuit 201 applies the OFF voltage of the TFT to the driving line 211, each pixel on the row returns to accumulation of charges. In this way, the drive circuit 201 sequentially drives the rows on the sensor array, and executes a scan, and the charges output from all the pixels are converted into digital values ultimately. This can read out radiation image data.

<Operation of Radiation Imaging System>

Figure 3B:
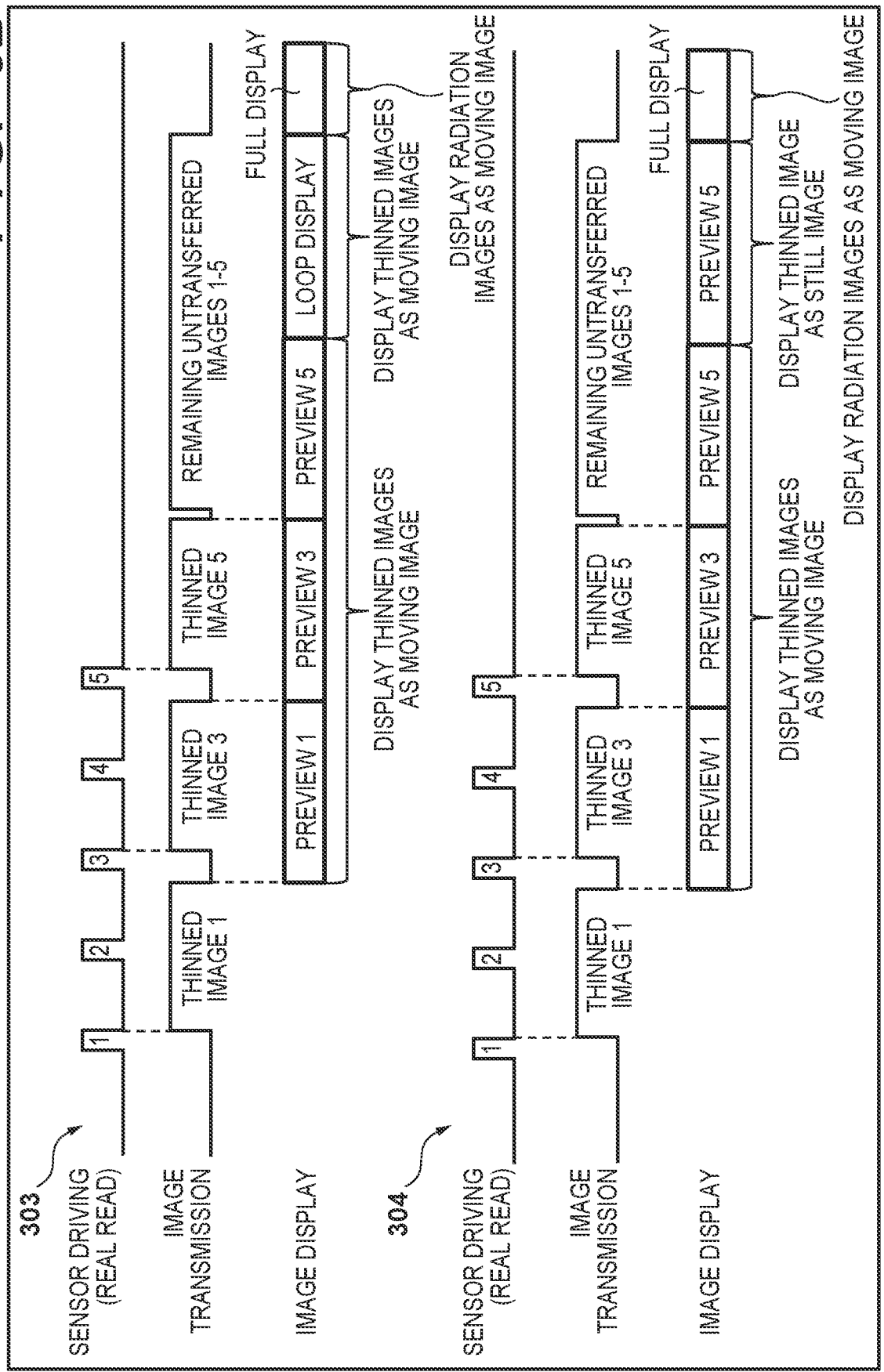
FIG. 3B is a timing chart showing an example of the imaging operation of the radiation imaging system according to the first embodiment.

An example of the operation of the overall radiation imaging system will be described next with reference to FIGS. 3A and 3B. FIGS. 3A and 3B are timing charts each showing an example of the operation of the radiation imaging system at the time of moving image capturing. An example when images can be transferred in real time will be described with reference to 301 and 302. A method of displaying images on the display device 114 during transfer of untransferred images is different between 301 and 302. In 301, loop display is performed. In 302, a still image is displayed. A case in which, for example, a communication speed is 100 Mbps or more although it depends on the resolutions of the images to be transferred is assumed as a case in which the images can be transferred in real time.

In 301 and 302, if an imaging request is turned on in a state in which imaging preparation is complete, the radiation source 109 starts radiation irradiation in synchronism with the timing of the radiation imaging apparatus 101. Upon receiving the radiation irradiation, the radiation imaging apparatus 101 performs sensor driving control at a predetermined timing, and obtains image data corresponding to the radiation irradiation. The obtained image data undergoes necessary image processing such as offset correction and thinning processing, and then preview images for preview display, that is, thinned images are transferred in real time.

In the example shown in FIG. 3A, the radiation imaging apparatus 101 sequentially transfers thinned images 1, 2, . . . , 5 in real time. After the real time transfer, the remaining untransferred images corresponding to the thinned images are transferred. For example, if ¼-size thinned images are transferred as preview images, after thinned images 1, 2, . . . are transferred, remaining ¾-size untransferred image 1 corresponding to thinned image 1, remaining ¾-size untransferred image 2 corresponding to thinned image 2, . . . , remaining ¾-size untransferred image 5 corresponding to thinned image 5 are sequentially transferred. In this way, a series of untransferred images are transferred in the same order as that of a series of transferred thinned images. This transfers all the original images.

The control apparatus 113 receives the thinned images of radiation images captured by the radiation imaging apparatus 101, and displays the thinned images as a moving image on the display device 114. After completion of the reception of the thinned images, the control apparatus 113 receives the remaining untransferred images obtained by excluding the thinned images from the radiation images. After the reception of the untransferred images, the control apparatus 113 displays the radiation images as a moving image on the display device 114. For example, the control apparatus 113 sequentially obtains thinned images 1, 2, . . . , 5, and performs preview displays 1, 2, . . . , 5 on the display device 114. Then, as shown in the example of 301, while the untransferred images are received, the control apparatus 113 performs loop reproduction to repeatedly display the received thinned images as the moving image on the display device 114. For example, while the remaining untransferred images are transferred from the radiation imaging apparatus 101, preview displays 1, 2, . . . , 5 undergo loop reproduction in that order. Upon completion of the transfer of the remaining untransferred images, the original images are stored while they are displayed in full size. As described above, while the untransferred images are received, the control apparatus 113 performs loop reproduction to repeatedly display the received thinned images as the moving image on the display device 114.

The control apparatus 113 may receive the untransferred images stepwise, and execute control to increase the resolution of an image stepwise by displaying, on the display device 114, as a moving image, images including the thinned images and received parts of the untransferred images.

For example, after transferring thinned images 1, 2, . . . , 5, the radiation imaging apparatus 101 transfers part of remaining untransferred image 1 corresponding to thinned image 1, part of remaining untransferred image 2 corresponding to thinned image 2, . . . , part of remaining untransferred image 5 corresponding to thinned image 5. Then, the radiation imaging apparatus 101 further transfers part of remaining untransferred image 1, part of remaining untransferred image 2, . . . stepwise. The control apparatus 113 performs loop reproduction to repeatedly display images including the thinned images and the received parts of the untransferred images on the display device 114. At this time, by receiving the untransferred images stepwise, it is possible to increase the resolution of the image stepwise at the time of loop reproduction.

As described above, it is possible to confirm the image in real time by preview display of the thinned image data, and also confirm a high-resolution image by displaying the original image data in full size later. By performing processing of increasing the resolution stepwise, it is possible to confirm a state in which the moving image gradually becomes fine.

Note that the full-size original images which have not been thinned out may be stored without being displayed. Then, the original images may be reproduced in response to a user operation.

As shown in the example of 302, while the untransferred images are received, the control apparatus 113 may continuously display, on the display device 114, the still image of the radiation image corresponding to the last received thinned image after display (preview display) of the thinned images as the moving image in response to reception of the untransferred image corresponding to the last received thinned image. That is, instead of performing loop reproduction of preview displays, preview display of the last transferred thinned image may be continued. For example, in the example shown in FIG. 3A, preview display 5 may be continued. At this time, remaining ¾-size untransferred image 5 corresponding to thinned image 5 may be transferred first, and then thinned image 5 may be replaced by full-size original image 5 corresponding to it. In this case, preview display 5 is continued on the display device 114 for a while after preview displays 1 to 5. Upon completion of transfer of remaining ¾-size untransferred image 5 corresponding to thinned image 5, the still image of full-size original image 5 is displayed.

Thinned image 5 may be replaced stepwise in accordance with transfer to increase the resolution instead of replacing thinned image 5 after completion of transfer of remaining ¾-size untransferred image 5 corresponding to thinned image 5. Then, when transfer of remaining 4/3 untransferred images corresponding to the remaining thinned images is complete, loop reproduction of the full-size original images may be performed.

An example of changing the transfer frame rate of the thinned images in accordance with a wireless communication status will be described next with reference to 303 and 304. 303 and 304 each show an example when the images cannot be transferred in real time. A method of displaying the images on the display device 114 during transfer of the untransferred images is different between 303 and 304. In 303, loop display is performed. In 304, a still image is displayed. In a wireless communication status in which the thinned images cannot be wirelessly transferred in real time, the transfer frame rate of the thinned images is decreased. A case in which, for example, a communication speed is lower than 100 Mbps although it depends on the resolutions of the images to be transferred is assumed as a case in which the images cannot be transferred in real time.

In the example shown in FIG. 3B, since the images cannot be transferred in real time, the transfer frame rate of the thinned images is decreased to transfer one frame per two frames. In image transfer, thinned images 1, 3, and 5 are sequentially transferred.

After this transfer processing, remaining untransferred images 1, 3, and 5 corresponding to thinned images 1, 3, and 5 and full-size original images 2 and 4 are transferred. For example, if ¼-size thinned images are transferred as preview images, after thinned images 1, 3, and 5 are transferred, remaining ¾-size untransferred image 1 corresponding to thinned image 1, original image 2, remaining ¾-size untransferred image 3 corresponding to thinned image 3, original image 4, and remaining ¾-size untransferred image 5 corresponding to thinned image 3 are sequentially transferred. This transfers all the original image data.

The display device 114 sequentially obtains thinned images 1, 3, and 5 under the control of the control apparatus 113, and performs preview displays 1, 3, and 5. Similar to 301, as shown in 303, while the remaining untransferred images are transferred from the radiation imaging apparatus 101 to the control apparatus 113, the preview displays may undergo loop reproduction. In this case, preview displays 1, 3, and 5 undergo loop reproduction. Note that as shown in 304, while the remaining untransferred images are transferred from the radiation imaging apparatus 101 to the control apparatus 113, preview display 5 of last transferred thinned image 5 may be continued. Upon completion of the transfer of the remaining untransferred images, the original images are stored while they are displayed in full size.

Note that in 303 and 304, the example of changing the transfer frame rate to a lower rate in accordance with the communication status has been explained. The sizes of the thinned images may be changed in accordance with the wireless communication status. More specifically, in the wireless communication status in which the thinned images cannot be wirelessly transferred in real time, the sizes of the thinned images may be changed to smaller sizes. If, for example, the communication speed is lower than 100 Mbps, smaller ⅛-size thinned images may be generated and transferred. This makes it possible to transfer the thinned images in real time. The remaining ⅞-size untransferred images are sequentially transferred later in the same manner. After completion of the transfer, the original images are displayed in full size.

In addition, whether to change the transfer frame rate or the sizes of the thinned images in accordance with the wireless communication status may be selectable by accepting a user operation. For example, in the wireless communication status in which the thinned images cannot be wirelessly transferred in real time, selection of whether to decrease the transfer frame rate of the thinned images or change the sizes of the thinned images to smaller sizes may be accepted.

Alternatively, the untransferred images may be transferred while no imaging is performed.

As described above, a radiation imaging apparatus (for example, 101) according to this embodiment includes an imaging unit (for example, 200) that captures a radiation image, a generation unit (for example, 102) that generates each of thinned images of a plurality of radiation images captured by the imaging unit, and a transfer unit (for example, 103, 108) that wirelessly transfers a plurality of thinned images, wherein after completion of the transfer of the plurality of thinned images, the transfer unit transfers each of remaining untransferred images obtained by excluding the thinned images from the radiation images. This makes it possible to display all the radiation images as a moving image at a transfer destination, thereby making it easy to confirm the radiation images whose image sizes are not reduced.

Furthermore, a control apparatus (for example, 113) according to this embodiment includes a reception unit that receives each of thinned images corresponding to a plurality of radiation images captured by an imaging unit, and a control unit that displays the plurality of thinned images as a moving image on a display device (for example, 114), wherein after completion of the reception of the plurality of thinned images, the reception unit receives each of remaining untransferred images obtained by excluding the thinned images from the radiation images, and after the reception of the untransferred images, the control unit displays the plurality of radiation images as a moving image on the display device. This makes it possible to display all the radiation images, thereby making it easy to confirm the radiation images whose image sizes are not reduced.

Second Embodiment

This embodiment will describe an example in which if a frame number capable of identifying an imaging ordinal number assigned to a captured radiation image matches a predetermined number, a thinned image corresponding to the frame number is transferred, and if the frame number does not match the predetermined number, the thinned image corresponding to the frame number is not transferred.

<Processing>

Figure 4A:
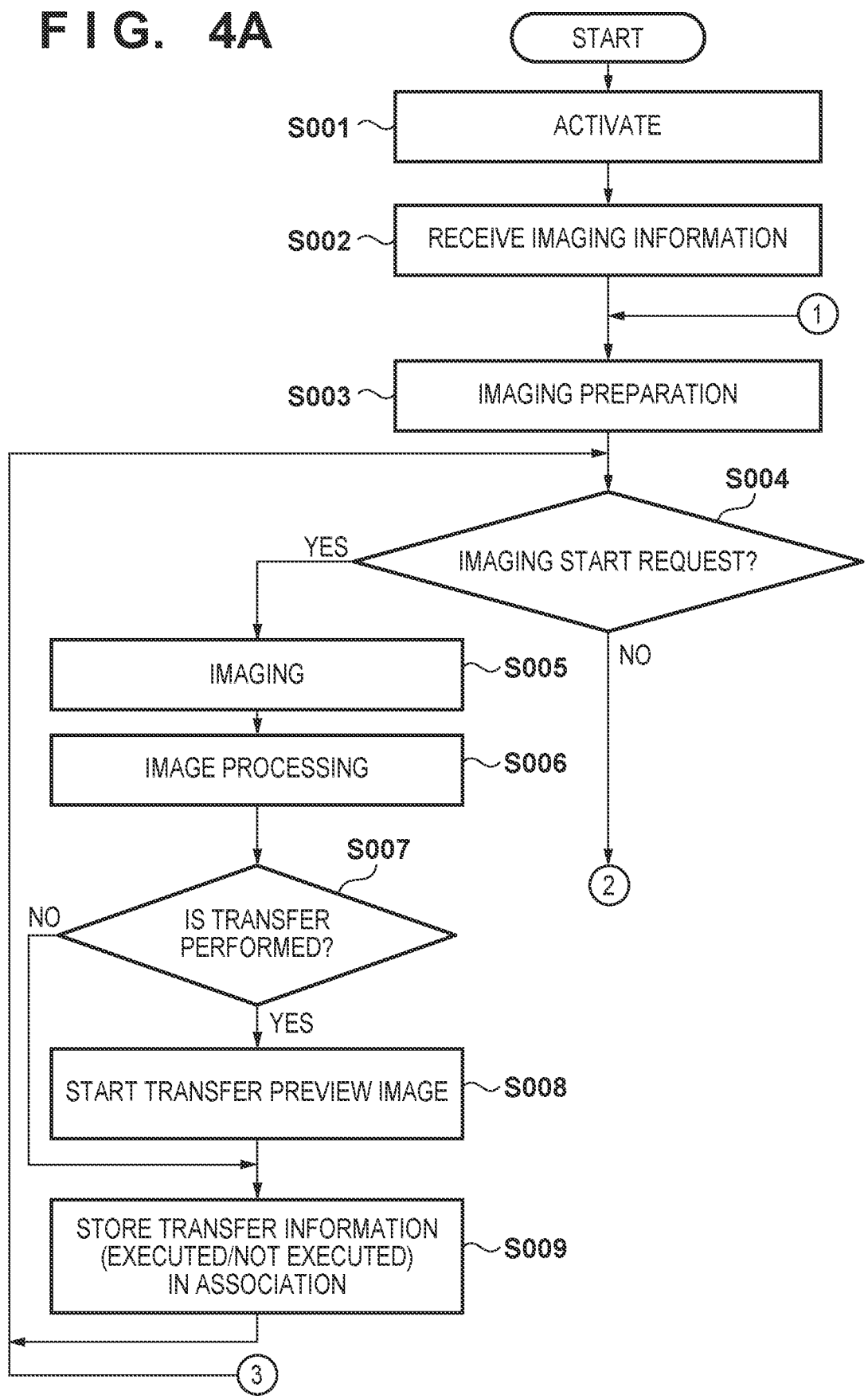
FIG. 4A is a flowchart illustrating the imaging operation of a radiation imaging apparatus according to the second embodiment.
Figure 4B:
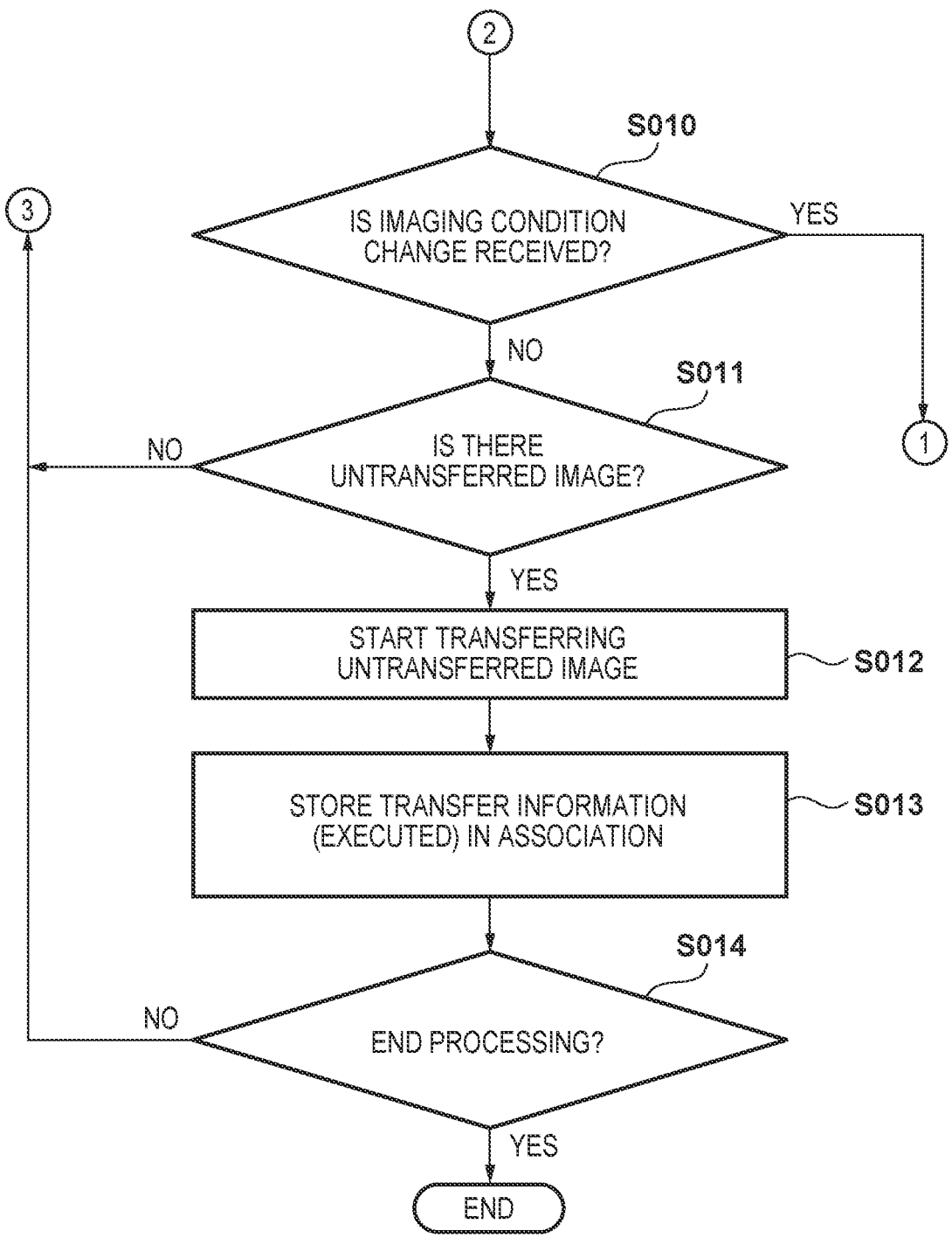
FIG. 4B is a flowchart illustrating the imaging operation of the radiation imaging apparatus according to the second embodiment.

A processing procedure at the time of imaging by a radiation imaging apparatus 101 according to the second embodiment will be described with reference to flowcharts shown in FIGS. 4A and 4B. In step S001, an imaging control unit 102 of the radiation imaging apparatus 101 performs, as activation processes, connection processing to a control apparatus 113 and the radiation generation control apparatus 110 and various setting processes. Next, the control apparatus 113 performs processing of inputting imaging information, and the imaging information is transmitted to the radiation imaging apparatus 101. The input imaging information includes information concerning a captured subject, information concerning a captured portion, information concerning radiation generation conditions, and information concerning imaging conditions for operating the radiation imaging apparatus 101. The radiation imaging apparatus 101 has a plurality of imaging modes shown in FIG. 5, and can operate in the plurality of imaging modes each having at least one of, for example, an image size parameter, a binning parameter, a frame rate parameter, and an output gain parameter.

In step S002, a wireless communication unit 103 of the radiation imaging apparatus 101 receives the imaging information. In step S003, the imaging control unit 102 (a driving control unit 106) selects the imaging mode corresponding to the imaging conditions included in the imaging information, and performs imaging preparation. In step S004, the imaging control unit 102 (driving control unit 106) determines whether a notification of an imaging start request is made. The radiation generation control apparatus 110 notifies the radiation imaging apparatus 101 of the imaging start request in response to the pressing of an irradiation switch or a fluoroscopy pedal connected to the radiation generation control apparatus 110.

If the notification of the imaging start request is made (YES in step S004), the process advances to step S005. On the other hand, if the notification of the imaging start request is not made (NO in step S004), that is, if the pressing of the irradiation switch or the fluoroscopy pedal is released or imaging of a designated number of frames defined by an imaging technique is complete, the process advances to step S010.

In step S005, the imaging control unit 102 (driving control unit 106) performs imaging in synchronism with a radiation irradiation timing of a radiation source 109, thereby obtaining a radiation image. In step S006, the imaging control unit 102 (an image processing unit 107) performs necessary image processing such as offset correction for the obtained radiation image, and stores the processed image in a storage unit 104.

In step S007, the imaging control unit 102 (transfer control unit 106) performs transfer determination processing of determining whether to instantaneously transfer the obtained image frame to the outside (step S007). Details of the transfer determination processing will be described later. If it is determined to execute transfer (YES in step S007), the process advances to step S008; otherwise (NO in step S007), the process advances to step S009.

Figures 5, 6:
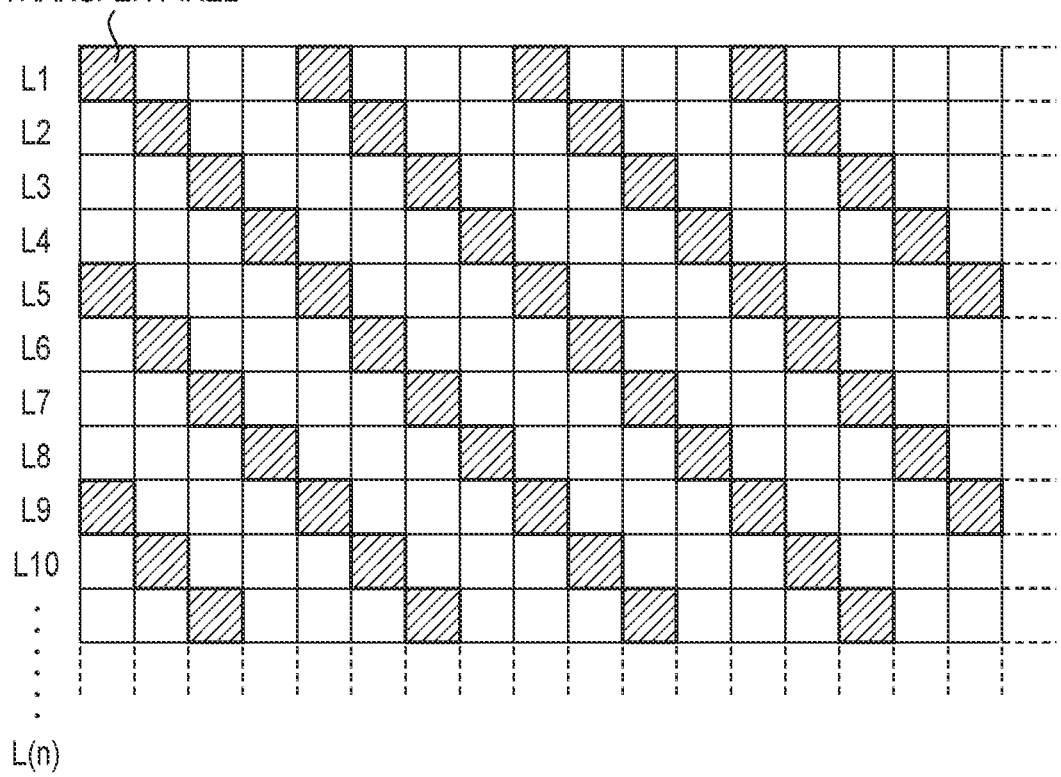
FIG. 5 is a table showing an example of an imaging mode table indicating the operation conditions of the radiation imaging apparatus.
FIG. 6 is a view showing an example of a thinning method at the time of generation of a thinned image.

In step S008, the imaging control unit 102 (transfer control unit 106) starts wireless transfer of a preview image corresponding to the obtained image. The preview image is thinned image data obtained by thinning out some pixels of the obtained image to reduce the obtained image. As a method of generating a preview image, there may be a method of using only pixels arranged in an oblique direction indicated by oblique lines at a unit of 4 pixels×4 pixels, as shown in FIG. 6. The present invention, however, is not limited to this. A thinning method may be changed, or a method of averaging a plurality of pieces of pixel information may be adopted. The image need not always be thinned out, and the entire obtained image may be transferred as a preview image. Alternatively, the thinning rate of the preview image may be changed in accordance with the imaging mode and the imaging technique or in accordance with the displayable resolution of a display device 114 used. The preview image need only have a size that allows at least a radiographer to grasp an imaging status.

In step S009, in accordance with a transfer execution status, the imaging control unit 102 (transfer control unit 106) stores transfer information in association with the frame image stored in the storage unit 104. If the preview image is transferred (YES in step S007), information indicating that transfer has been executed is associated with the frame image; otherwise (NO in step S007), the frame image and information indicating that no transfer has been executed are stored in association with each other. Note that the example of associating the transfer information with the frame image (step S009) has been explained as a step after the start of the preview image transfer (step S008). However, upon receiving a preview image transfer completion notification, the information indicating that transfer has been executed may be associated with the frame image. After that, the process returns to step S004.

Note that the preview image transfer itself may be performed during imaging of a plurality of frames, and the imaging control unit 102 of the radiation imaging apparatus 101 may actually shift the process to control of imaging of the next frame without waiting for completion of the preview image transfer (the process returns to step S004). When transferring the image, noise may be generated in the obtained image due to the influence of a radio wave generated at the time of wireless communication. Therefore, control may be performed to temporarily stop the image transfer during a readout period in which the image data is obtained and then restart the subsequent image transfer after completion of the readout processing.

As described above, while the imaging start request is made, the above-described steps (S004 to S009) are repeatedly performed, thereby executing moving image capturing and continuous capturing.

In step S010, the imaging control unit 102 determines whether the wireless communication unit 103 receives an imaging condition change instruction. If an imaging condition change instruction is received (YES in step S010), the process returns to step S003, and the operation is switched to an operation corresponding to the changed imaging conditions to perform another imaging technique, and imaging preparation is performed again; otherwise (NO in step S010), the process advances to step S011.

In step S011, with reference to the pieces of transfer information of the plurality of frame images stored in the storage unit 104, the imaging control unit 102 (a transfer control unit 108) determines whether there are untransferred image data. If there are untransferred image data (YES in step S011), the process advances to step S012; otherwise (NO in step S011), the process returns to step S004.

In step S012, the imaging control unit 102 (transfer control unit 108) sequentially starts to transfer image data of the corresponding frames. For frames transferred as preview images by thinning out some pixel data of each image, the remaining pixel data not used to transfer the preview images are transferred. However, all the data of the frame images including the pixels used for the preview images may be transferred, as a matter of course.

In step S013, when transfer of all the data of the corresponding frames is complete, the imaging control unit 102 (transfer control unit 108) stores, in association with each of the corresponding frame images, information indicating that transfer has been executed.

In step S014, the imaging control unit 102 determines whether to end the imaging processing. If the imaging processing ends by an operation of, for example, turning off the power, the series of processes directly ends; otherwise, the process returns to step S004.

Note that in this flowchart, for the sake of convenience, the step (step S013) of associating the transfer information (the information indicating that transfer has been executed) of each image is performed after the start of transfer of the untransferred images. However, the step of associating the transfer information may be performed after completion of transfer of the corresponding frame. Before completion of transfer of the untransferred images, the process may return to the step (step S004 after NO is determined in step S014) of confirming an imaging request so as to accept the next imaging request.

<Operation of Overall Radiation Imaging System>

Figure 7:
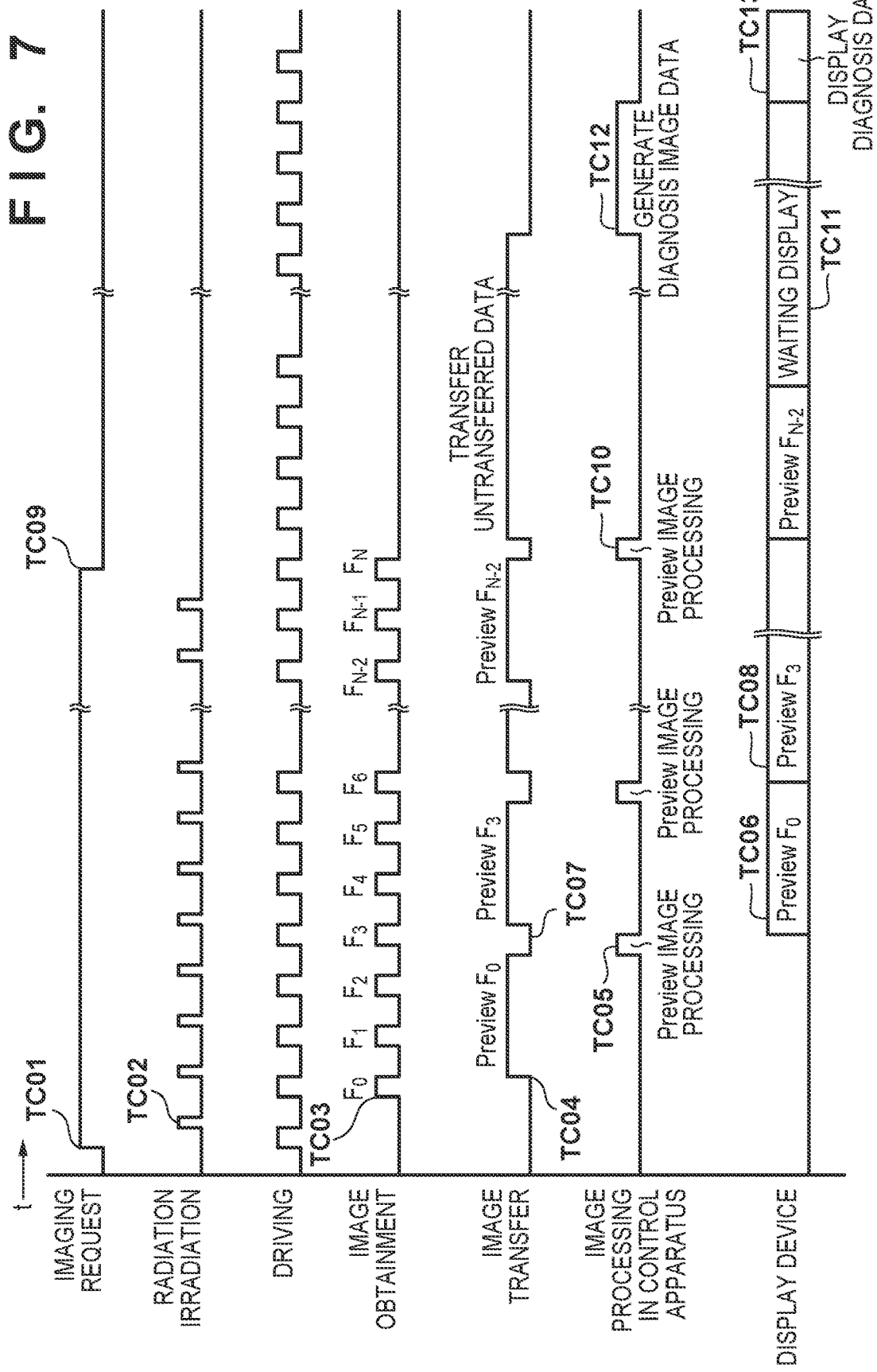
FIG. 7 is a timing chart showing an example of the imaging operation of a radiation imaging system according to the second embodiment.

An example of the operation of the overall radiation imaging system will be described next with reference to FIG. 7. FIG. 7 is a timing chart showing an example of the operation of the radiation imaging system including the radiation imaging apparatus 101, the radiation generation control apparatus 110, the control apparatus 113, and the display device 114 at the time of moving image capturing.

If an imaging request is turned on (TC01) in a state in which the imaging preparation under given imaging conditions is complete, the radiation source 109 starts (TC02) radiation irradiation in synchronism with the timing of the radiation imaging apparatus 101. Note that in this example, radiation irradiation is performed by pulse irradiation for each imaging frame. However, in some cases, radiation irradiation may be continuously performed. Upon receiving the radiation irradiation, the radiation imaging apparatus 101 performs driving control at a predetermined timing, and obtains (TC03) image data (F0) corresponding to the radiation irradiation (TC02). Transfer determination processing of determining whether to perform, in real time, preview transfer of the obtained image data having undergone necessary image processing such as offset correction. Note that in this timing chart, "transfer execution" is determined every three frames (F0, F3, F6, . . . ).

If "transfer execution" is determined in the transfer determination processing of obtained image data F0, transfer of a preview image corresponding to F0 starts (TC04). While the preview image is transferred, the radiation imaging apparatus 101 and the radiation generation control apparatus 110 synchronously execute imaging at the frame rate of the designated imaging conditions. In this case, since "transfer non-execution" is determined for obtained frames F1 and F2 in the transfer determination processing, the frames are stored in the storage unit 104 of the radiation imaging apparatus 101 without transferring preview images. Upon completion of reception of preview image F0, the control apparatus 113 performs (TC05) necessary image processing for displaying the preview image, and displays (TC06) the thus obtained image on the display device 114.

Similarly, if "transfer execution" is determined in the transfer determination processing of obtained image data F3, transfer of a preview image corresponding to F3 starts (TC07). Upon completion of reception of preview image F3, the control apparatus 113 performs necessary image processing for preview, and updates (TC08) the preview image from F0 to F3 to be displayed on the display device 114.

After repeating the moving imaging operation in this way, the imaging request is turned off (TC09) upon the end of imaging. Upon completion of the transfer of the preview images, untransferred images are sequentially transferred (TC10) with reference to pieces of transfer information of the respective images stored in the storage unit 104. Upon completion of display of last preview image F(N-2), the control apparatus 113 shifts to a state in which it waits for transfer of the remaining data, and thus switches display contents on the display device 114 to waiting display. In waiting display, for example, a progress bar indicating the progress state of reception of the remaining data may be displayed on the screen. Alternatively, a preview moving image may be reproduced and displayed using only received preview images. The last obtained preview image may be continuously displayed. In response to reception of untransferred image data, the display contents may sequentially be updated and displayed. At least one or a plurality of these methods may be used in combination to perform display. The display screen may be switched in accordance with input from an input device 115.

Upon completion of reception of all the image data of a series of continuous imaging operations, the control apparatus 113 generates (TC12) diagnosis image data corresponding to the imaging operations. Upon completion of the generation, the generated diagnosis data are displayed (TC13) on the display device 114. In the case of, for example, tomosynthesis imaging, the generation of the diagnosis image data indicates generation of three-dimensional diagnosis image data reconstructed based on the obtained image data captured with a plurality of position relations. In the case of long-length imaging, the generation of the diagnosis image data indicates generation of long-length imaging data by combining the plurality of obtained image data. If a moving image of expansion/contraction of respiratory organs, the swallowing movement of digestive organs, or the like is captured, a moving image may be reproduced in a state in which frame images lacking in preview images are interpolated.

Note that this timing flowchart shows an example of obtaining an image by performing radiation irradiation for each frame at the time of moving image capturing. The present invention, however, is not limited to this. For example, control may be executed to obtain captured image frames by performing radiation irradiation once per a predetermined number of driving operations.

<Transfer Determination Processing>

Details of the transfer determination processing during imaging in step S007 of FIGS. 4A and 4B will be described next. In this embodiment, transfer execution is determined when a frame number at the time of continuous imaging of a moving image or the like matches a predetermined specific transfer execution frame number (predetermined number).

Figures 8, 9:
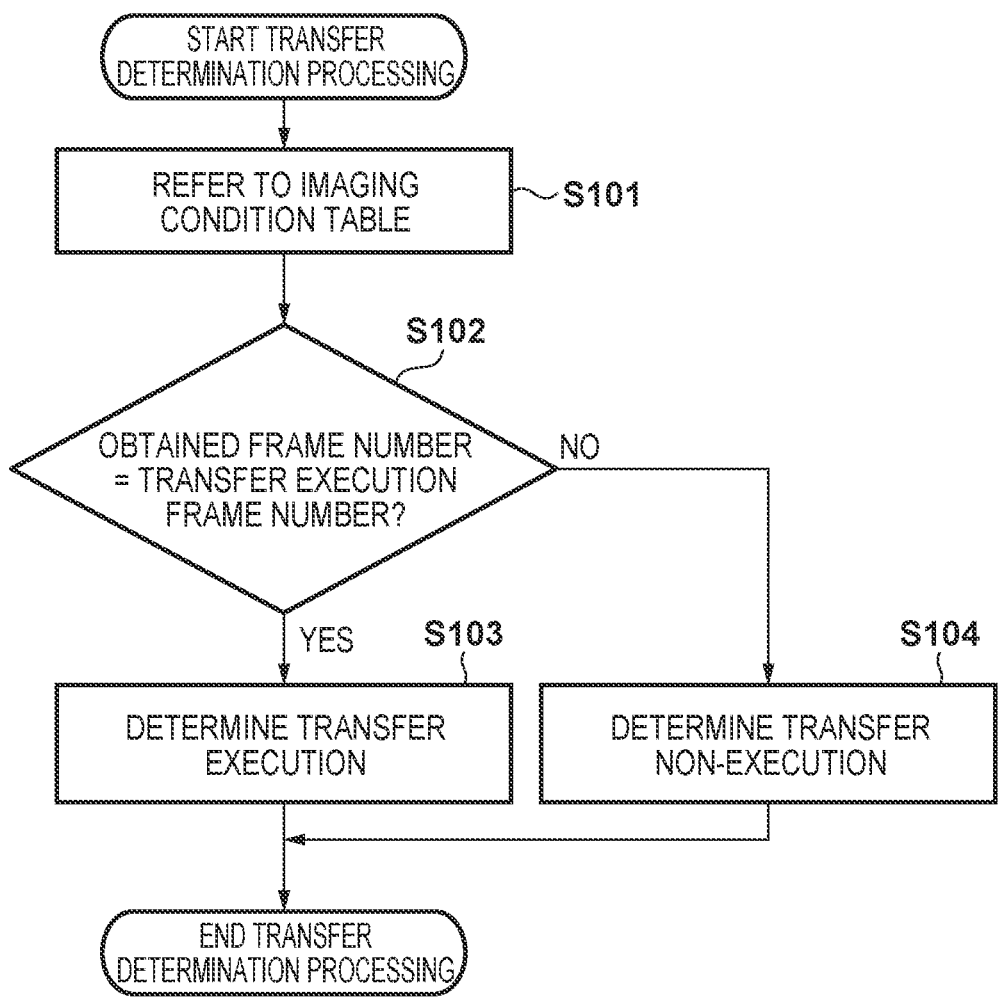
FIG. 8 is a table showing an example of a table in which a transfer frame number is defined according to the second embodiment.
FIG. 9 is a flowchart illustrating a processing procedure according to the second embodiment.

The transfer execution frame number (predetermined number) is, for example, a number defined for each imaging technique or a number defined for each imaging mode. As shown in FIGS. 4A and 4B, the radiation imaging apparatus 101 has the plurality of imaging modes, and the appropriate imaging mode is used in accordance with the imaging technique. For example, if it is defined to use imaging mode No. 2 for imaging technique A, imaging mode No. 5 for imaging technique B, and imaging mode No. 1 for imaging technique C, an imaging condition table shown in FIG. 8 is stored in the storage unit 104. In this case, the transfer execution frame number can be defined in advance in accordance with the imaging technique as in a preview transfer execution frame number item of FIG. 8. If, for example, imaging technique A is selected, when the frame number at the time of imaging is 0, 15, 30, 45, or 60, transfer execution is determined. Note that in this example, the frame number is defined to start with 0 but is not limited to this. For example, the frame number may start with another number such as 1.

As described above, in the case of a technique of capturing several tens images while changing the position and direction, such as tomosynthesis imaging, an imaging status need only be confirmed for each of timings which are separated from each other to some extent in a position relation. To do this, for example, an interval is defined like the frame numbers 0, 15, 30, 45, and 60. If only several images are captured like long-length imaging, a frame to undergo preview transfer can be defined in accordance with the imaging technique. For example, it is defined to perform preview transfer of only frame number 0.

Note that the imaging technique has been exemplified but the present invention is not limited to this. For example, a preview transfer execution frame number may be defined based on the frame rate or image size information as a parameter included in the imaging mode. For example, the interval of the transfer execution frame number may be defined larger for the mode in which the frame rate is higher, and the interval of the transfer execution frame number may be defined smaller for the mode in which the frame rate is lower. Furthermore, the transfer execution frame numbers need not always be registered as all frame numbers in the table. For example, information indicating "every 10 frames" or information indicating transfer at "1 fps" may be defined.

The pieces of information of the imaging condition table need not be fixed values, and the setting values may be variable in accordance with, for example, an instruction from the control apparatus 113. For example, it can be defined to transfer, as a preview image, only one frame at the start of imaging by defining to determine transfer execution for only frame number 0 in all the imaging modes.

The procedure of the transfer determination processing according to this embodiment will be described with reference to a flowchart shown in FIG. 9. In step S101, when performing the transfer determination processing, the imaging control unit 102 (transfer control unit 108) refers to the current imaging condition table. In step S102, the imaging control unit 102 (transfer control unit 108) determines whether the frame number obtained this time matches the defined transfer execution frame number by comparing the frame numbers with each other. If the frame numbers match each other (YES in step S102), the imaging control unit 102 (transfer control unit 108) determines transfer execution in step S103; otherwise (NO in step S102), the imaging control unit 102 (transfer control unit 108) determines transfer non-execution in step S104.

If a frame number capable of identifying an imaging ordinal number assigned to a captured radiation image matches a predetermined number, the radiation imaging apparatus according to this embodiment transfers a thinned image corresponding to the frame number, and if the frame number does not match the predetermined number, the radiation imaging apparatus does not transfer the thinned image corresponding to the frame number.

This makes it possible to simply confirm the imaging status in real time. Even if a setting error of radiation irradiation conditions or an alignment error of an object/grid or the like occurs, imaging can be immediately interrupted to shift to re-imaging. It is also possible to define a preview image transfer frequency suitable for the imaging technique or the imaging mode.

Third Embodiment

The third embodiment will describe an example of controlling transfer of a thinned image in accordance with the wireless communication state of a wireless communication unit to be used to transfer the thinned images. For example, control is executed to transfer a thinned image if the wireless communication unit to be used to transfer the thinned image is not transferring another thinned image and not to transfer the thinned image if the wireless communication unit is transferring another thinned image. An example of the arrangement of a radiation imaging system and an operation procedure at the time of moving image capturing are the same as in the first embodiment. A transfer control unit 108 in a radiation imaging apparatus 101 according to this embodiment can confirm the state of a wireless communication unit 103 and confirm the execution state of wireless transfer of an image.

<Transfer Determination Processing>

Figure 10:
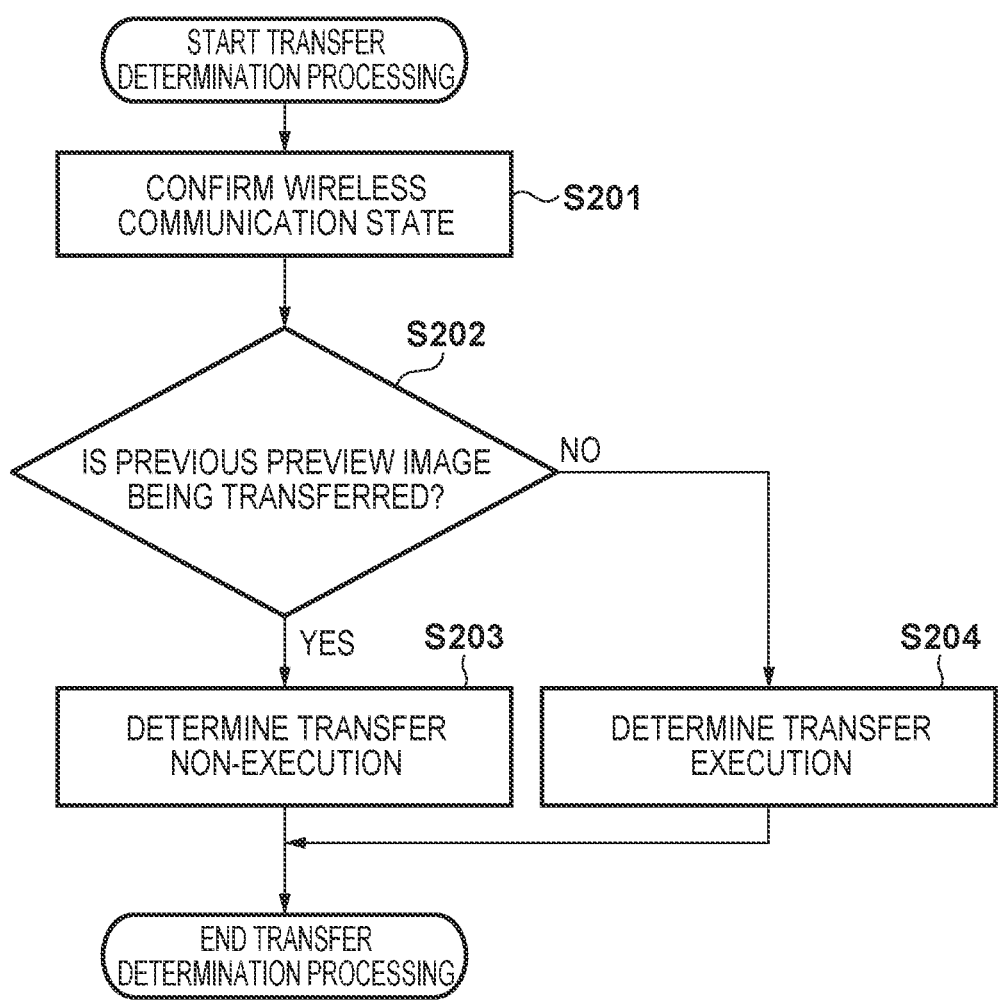
FIG. 10 is a flowchart illustrating a processing procedure according to the third embodiment.

The procedure of transfer determination processing according to this embodiment will be described with reference to a flowchart shown in FIG. 10. In step S201, the transfer control unit 108 confirms the current wireless communication state. In step S202, the transfer control unit 108 determines whether a preview image of a previously obtained frame is being transferred. If the preview image is being transferred (YES in step S202), the process advances to step S203; otherwise (NO in step S202), the process advances to step S204. In step S203, the transfer control unit 108 determines transfer non-execution of the currently obtained frame. In step S204, the transfer control unit 108 determines transfer execution of the currently obtained frame. The series of processes then ends.

According to this embodiment, it is unnecessary to prepare in advance a transfer frame number definition table according to an imaging technique and an imaging mode. In addition, even if there is a variation in communicable speed depending on a wireless communication environment, it is possible to confirm a preview image at a possible speed corresponding to an environment in real time.

Fourth Embodiment

The fourth embodiment will explain an example of confirming a wireless communication status in the same manner as in the third embodiment, obtaining the current wireless communication execution speed, deciding the transfer frame rate of a preview image based on the obtained wireless communication speed, and performing transfer determination processing for an obtained frame every time. For example, control is executed not to transfer a thinned image if an elapsed time since the last execution of transfer of a thinned image does not exceed a period of a transfer frame rate. If the elapsed time since the last execution of transfer of the thinned image exceeds the period of the transfer frame rate and a wireless communication unit to be used to transfer a thinned image is not transferring another thinned image, control is executed to transfer the thinned image. Note that an example of the arrangement of a radiation imaging system and an operation procedure at the time of moving image capturing are the same as in the first and third embodiments. A transfer control unit 108 in a radiation imaging apparatus 101 according to this embodiment can confirm the state of a wireless communication unit 103 and confirm the execution state of wireless transfer of an image and a wireless communication speed.

<Transfer Determination Processing>

Figure 11:
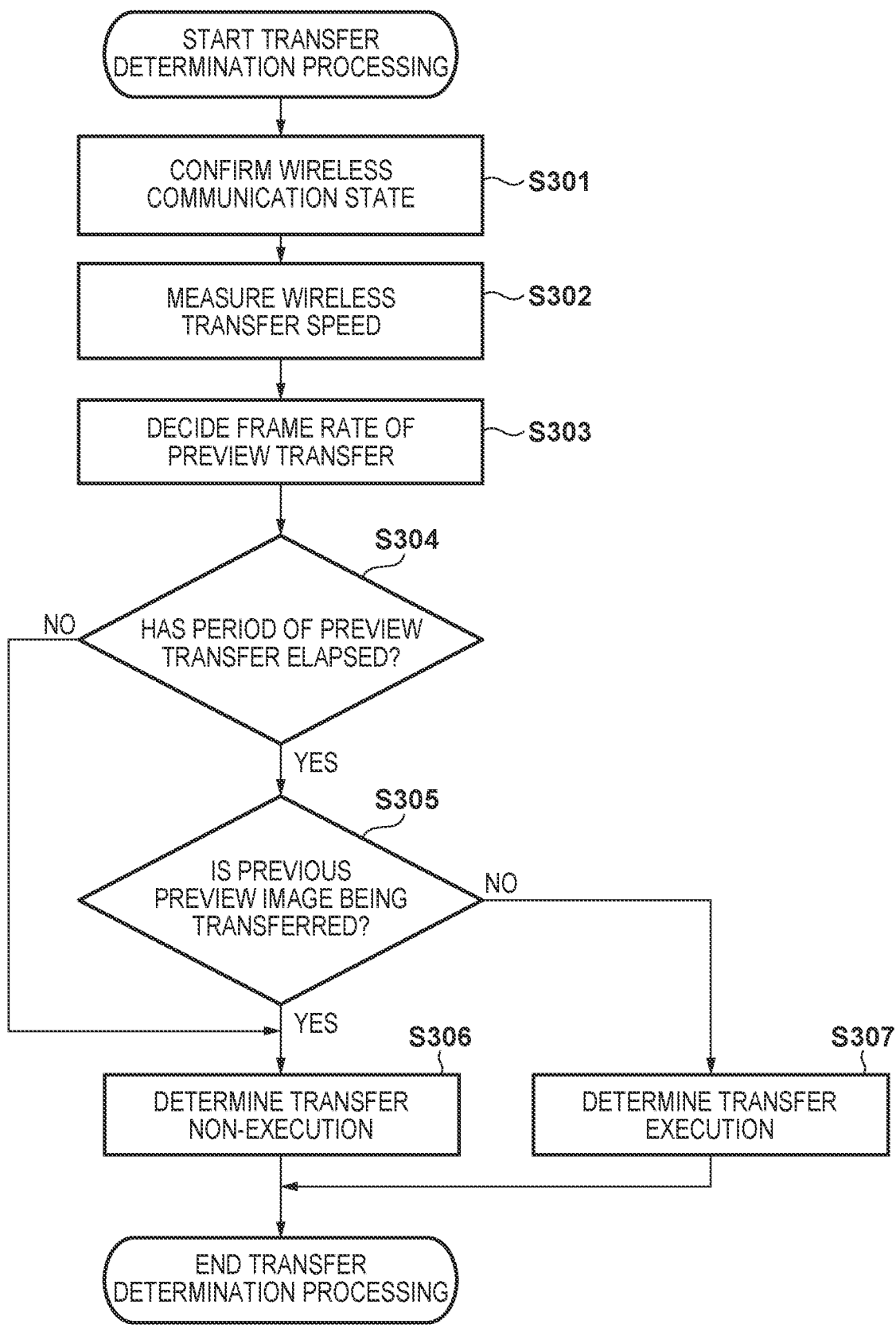
FIG. 11 is a flowchart illustrating a processing procedure according to the fourth embodiment.

The procedure of transfer determination processing according to this embodiment will be described with reference to a flowchart shown in FIG. 11. In step S301, the transfer control unit 108 confirms the current wireless communication state when performing transfer determination. In step S302, the transfer control unit 108 measures the current wireless communication speed.

In step S303, the transfer control unit 108 decides the frame rate of preview image transfer based on the measured wireless communication speed. The frame rate of preview image transfer is decided within a transferable range based on wireless communication speed information and size information of a preview image to be transferred in the current imaging mode.

Note that if the frame rate in the current imaging mode is Fps1 and the frame rate of the preview image is Fps2, the frame rate is decided within a range that satisfies Fps1≥Fps2. If the wireless communication speed is sufficient or the frame rate in the current imaging mode is low, Fps1=Fps2 is obtained and it is possible to transfer preview images of all frames in real time.

After the frame rate of the preview image is decided in step S303, in step S304 the transfer control unit 108 confirms the elapsed time since the last execution of preview transfer, and determines whether the elapsed time exceeds the period of the preview image transfer frame rate. If the elapsed time has not reached the period of the preview transfer frame rate (NO in step S304), the process advances to step S306. On the other hand, if the elapsed time exceeds the period of the preview transfer frame rate (YES in step S304), the process advances to step S305.

In step S305, the transfer control unit 108 determines whether the previous preview image is being transferred. If the previous preview image is being transferred (YES in step S305), the process advances to step S306; otherwise (NO in step S305), the process advances to step S307.

In step S306, the transfer control unit 108 determines transfer non-execution of the currently obtained frame. In step S307, the transfer control unit 108 determines transfer execution of the currently obtained frame. The series of processes then ends.

According to this embodiment, it is possible to perform preview transfer at an appropriate frame rate according to the current wireless communication environment by confirming the wireless communication speed in advance to decide the preview image transfer frame rate. Furthermore, even if the wireless communication speed temporarily lowers, it is possible to dynamically adjust the frame rate to transfer the preview image by confirming the communication speed for each obtained frame.

In addition, if transfer of the preview image for which transfer execution is determined last does not end due to instantaneous deterioration of the wireless environment, by determining transfer non-execution for the next preview image, it is possible to prevent the recognizability in real time from deteriorating by storing unnecessary transfer requests.

Fifth Embodiment

The fifth embodiment will describe an example in which a radiation imaging apparatus 101 is used by being mounted on a support whose position is slidable. In this embodiment, with reference to the positional relationship between a radiation source and the radiation imaging apparatus at the time of imaging, preview image transfer determination is performed based on the positional relationship. For example, if the positional relationship between the radiation imaging apparatus and the radiation source that irradiates the radiation imaging apparatus with radiation does not satisfy a predetermined positional relationship, control is executed not to transfer a thinned image. Note that the same reference numerals as in the first embodiment denote the same components as those described in the first embodiment.

Figure 12:
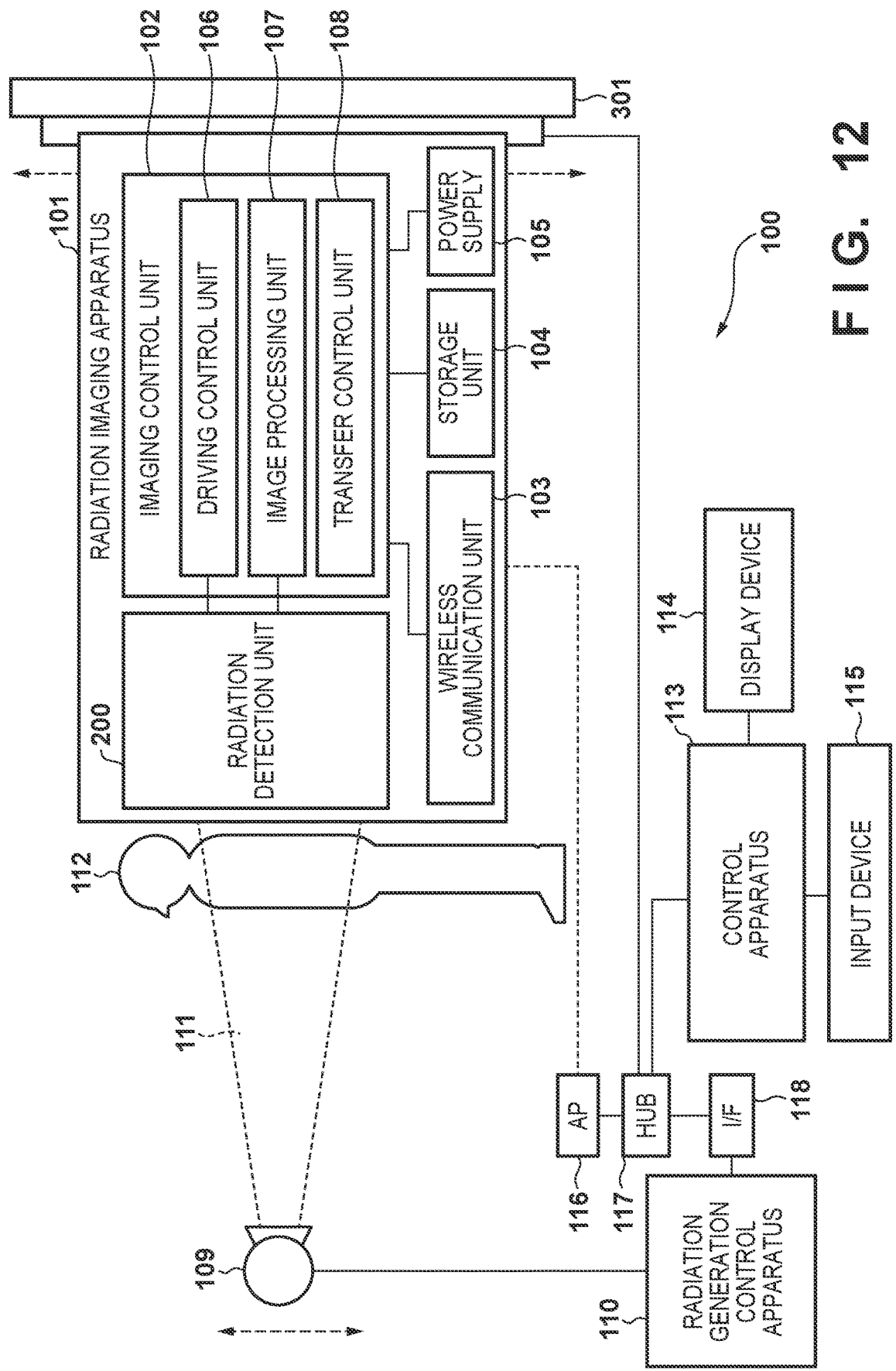
FIG. 12 is a view showing an example of the arrangement of a radiation imaging system according to the fifth embodiment.

FIG. 12 shows an example of the schematic arrangement of a radiation imaging system 300 according to the fifth embodiment. In this embodiment, the radiation imaging apparatus 101 is mounted on a support 301. It is possible to move the position of the radiation imaging apparatus 101 by sliding the mounted position on the support 301 in accordance with an instruction from a control apparatus 113.

Assume that the support 301 is connected to the radiation imaging apparatus 101 by a cable such as Ethernet, and can communicate with the control apparatus 113 via a HUB 117. Note that Ethernet is merely an example, and communication may be performed by connection using another dedicated cable. In this case, for example, the support 301 and the control apparatus 113 may be connected directly. Note that the support 301 may be in, for example, a form of a bed table or a form of a vertical stand.

A radiation source 109 according to this embodiment can change the position of the radiation source 109 and an angle in the irradiation direction in accordance with imaging in response to an instruction from a radiation generation control apparatus 110. Furthermore, the radiation imaging apparatus 101 can obtain the positional relationship between the radiation source 109 and the radiation imaging apparatus 101 at the time of imaging by communication with the control apparatus 113 or the radiation generation control apparatus 110.

As an obtaining method, there is provided a method of periodically making a notification of a command including position information from the control apparatus 113 or the radiation generation control apparatus 110 when, for example, controlling to change the position of the radiation source 109 or the radiation imaging apparatus 101. The present invention is not limited to this, and the radiation imaging apparatus 101 may inquire of the control apparatus 113 about each positional relationship periodically or at an arbitrary timing. Note that the remaining components of the system and an operation procedure at the time of imaging are the same as in the first embodiment.

<Transfer Determination Processing>

Figure 13:
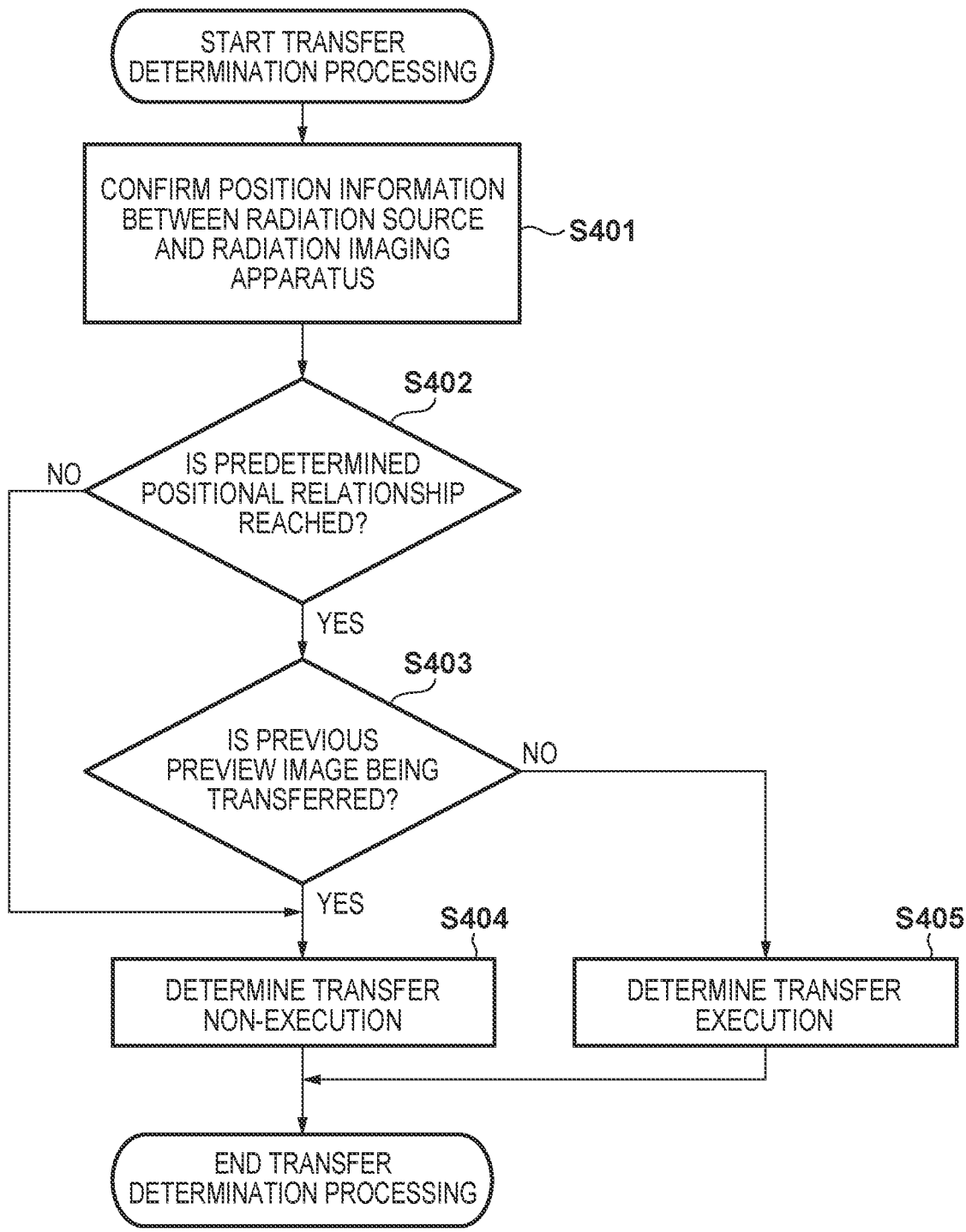
FIG. 13 is a flowchart illustrating a processing procedure according to the fifth embodiment.

Subsequently, the procedure of transfer determination processing according to this embodiment will be described with reference to a flowchart shown in FIG. 13. In step S401, when performing transfer determination, a transfer control unit 108 in the radiation imaging apparatus 101 obtains and confirms information of the positional relationship between the radiation source 109 and the radiation imaging apparatus 101. After that, in step S402, the transfer control unit 108 determines whether the radiation source 109 and the radiation imaging apparatus 101 have reached the predetermined positional relationship in a storage unit 104 or the like. If the predetermined positional relationship has been reached (YES in step S402), the process advances to step S403; otherwise (NO in step S402), the process advances to step S404.

In step S403, the transfer control unit 108 determines whether the previous preview image is being transferred. If the previous preview image is being transferred due to, for example, deterioration of the wireless communication environment (YES in step S403), the process advances to step S404; otherwise (NO in step S403), the process advances to step S405. In step S404, the transfer control unit 108 determines transfer non-execution of the currently obtained frame. In step S405, the transfer control unit 108 determines transfer execution of the currently obtained frame. The series of processes then ends. According to this embodiment, in the case of, for example, tomosynthesis imaging of capturing a plurality of frames while moving the radiation source 109 or the radiation imaging apparatus 101, it is possible to selectively confirm a captured frame from a specific angle in real time. Furthermore, in the case of long-length imaging of performing imaging a plurality of times or the like, it is possible to confirm a specific imaging position in real time.

According to the present invention, it is possible to display a plurality of thinned images as a moving image, and display, as a moving image, a plurality of radiation images whose image sizes are not reduced.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. A radiation imaging apparatus, comprising:
an imaging unit configured to obtain a plurality of radiation images as a moving image by performing imaging a plurality of times;
a generation unit configured to generate each of thinned images of the plurality of radiation images obtained as the moving image by the imaging unit; and
a transfer unit configured to wirelessly transfer a plurality of thinned images in real time, wherein
the transfer unit transfers each of remaining untransferred images obtained by excluding each of the thinned images corresponding to each of the radiation images from each of the radiation images after completion of the transfer of the plurality of thinned images.

2. The radiation imaging apparatus according to claim 1, wherein the transfer unit transfers the plurality of untransferred images in the same order as an order of transfer of the plurality of thinned images.

3. The radiation imaging apparatus according to claim 1, wherein the transfer unit changes a transfer frame rate of the plurality of thinned images in accordance with a wireless communication status.

4. The radiation imaging apparatus according to claim 3, wherein in a wireless communication status in which it is not possible to wirelessly transfer the plurality of thinned images in real time, the transfer unit decreases the transfer frame rate of the plurality of thinned images.

5. The radiation imaging apparatus according to claim 1, wherein the transfer unit transfers the plurality of thinned images whose sizes have been respectively changed in accordance with the wireless communication status.

6. The radiation imaging apparatus according to claim 5, wherein in a wireless communication status in which it is not possible to wirelessly transfer the plurality of thinned images in real time, the transfer unit transfers the plurality of thinned images whose sizes have been respectively changed to smaller sizes.

7. The radiation imaging apparatus according to claim 1, further comprising an acceptance unit configured to accept, in a wireless communication status in which it is not possible to wirelessly transfer the plurality of thinned images in real time, selection of whether to decrease a transfer frame rate of the plurality of thinned images or change sizes of the plurality of thinned images to smaller sizes.

8. The radiation imaging apparatus according to claim 1, wherein if a frame number capable of identifying an imaging ordinal number assigned to each of the plurality of radiation images matches a predetermined number, the transfer unit transfers a thinned image corresponding to the frame number among the plurality of thinned images, and if the frame number does not match the predetermined number, the transfer unit does not transfer the thinned image corresponding to the frame number among the plurality of thinned images.

9. The radiation imaging apparatus according to claim 8, wherein the predetermined number is defined by the imaging unit for each imaging technique.

10. The radiation imaging apparatus according to claim 8, wherein the radiation imaging apparatus is configured to operate in a plurality of imaging modes each having at least one of an image size parameter, a binning parameter, a frame rate parameter, and an output gain parameter, and
the predetermined number is defined for each imaging mode.

11. The radiation imaging apparatus according to claim 1, wherein if a wireless communication unit to be used to transfer the plurality of thinned images is not transferring a thinned image among the plurality of thinned images, the transfer unit transfers another thinned image among the plurality of thinned images, and
if the wireless communication unit is transferring the thinned image, the transfer unit does not transfer the other thinned image.

12. The radiation imaging apparatus according to claim 1, wherein the transfer unit does not transfer the thinned image if an elapsed time since last execution of transfer of the thinned image does not exceed a period of a transfer frame rate.

13. The radiation imaging apparatus according to claim 12, wherein the transfer unit transfers the thinned image if the elapsed time since the last execution of the transfer of the thinned image exceeds the period of the transfer frame rate and a wireless communication unit to be used to transfer the thinned image is not transferring another thinned image.

14. The radiation imaging apparatus according to claim 1, wherein the transfer unit does not transfer the plurality of thinned images if a positional relationship between the radiation imaging apparatus and a radiation source configured to irradiate the radiation imaging apparatus with radiation does not satisfy a predetermined positional relationship.

15. The radiation imaging apparatus according to claim 1, wherein the transfer unit transfers the plurality of untransferred images during a period in which the imaging unit does not perform imaging.

16. A control apparatus, comprising:
a reception unit configured to wirelessly receive each of thinned images in real time corresponding to a plurality of radiation images obtained by imaging unit that is configured to obtain a plurality of radiation images as a moving image by performing imaging a plurality of times; and
a control unit configured to display the plurality of thinned images as a moving image on a display device, wherein
the reception unit receives each of remaining untransferred images obtained by excluding each of the thinned images corresponding to each of the radiation images from each of the radiation images after completion of the reception of the plurality of thinned images, and
the control unit displays the plurality of radiation images as a moving image on the display device after the reception of the untransferred images.

17. The control apparatus according to claim 16, wherein the imaging unit changes a transfer frame rate or sizes of the plurality of thinned images in accordance with a wireless communication status.

18. The control apparatus according to claim 16, wherein during the reception of the plurality of untransferred images, the control apparatus performs loop reproduction to repeatedly display the received thinned images as the moving image on the display device.

19. The control apparatus according to claim 16, wherein the reception unit receives the plurality of untransferred images stepwise, and
the control unit executes control to increase a resolution of an image stepwise by displaying, as a moving image, images including the thinned images and received parts of the plurality of untransferred images.

20. The control apparatus according to claim 16, wherein during the reception of the plurality of untransferred images, in response to the reception of the untransferred image corresponding to the last received thinned image, the control unit continuously displays on the display device a still image of the radiation image corresponding to the last received thinned image after displaying the plurality of thinned images as the moving image.

21. A control method for a radiation imaging apparatus including an imaging unit configured to obtain a plurality of radiation images as a moving image by performing imaging a plurality of times, the method comprising:
generating each of thinned images of the plurality of radiation images obtained as the moving image by the imaging unit; and
wirelessly transferring a plurality of thinned images in real time, wherein
in the transferring, each of remaining untransferred images obtained by excluding each of the thinned images corresponding to each of the radiation images from each of the radiation images is transferred after completion of the transfer of the plurality of thinned images.

22. A control method for a control apparatus, comprising:
wirelessly receiving in real time each of thinned images corresponding to a plurality of radiation images obtained by an imaging unit that is configured to obtain a plurality of radiation images as a moving image by performing imaging a plurality of times; and
displaying the plurality of thinned images as a moving image on a display device, wherein
in the receiving, each of remaining untransferred images obtained by excluding each of the thinned images corresponding to each of the radiation images from each of the radiation images is received after completion of the reception of the plurality of thinned images, and
in the displaying, after the reception of the untransferred images, the plurality of radiation images are displayed as a moving image on the display device.

23. A non-transitory computer-readable storage medium storing a computer program for causing a computer to execute a control method for a radiation imaging apparatus including an imaging unit configured to obtain a plurality of radiation images as a moving image by performing imaging a plurality of times, the method comprising:
generating each of thinned images of the plurality of radiation images obtained as the moving image by the imaging unit; and
wirelessly transferring a plurality of thinned images in real time, wherein
in the transferring, each of remaining untransferred images obtained by excluding each of the thinned images corresponding to each of the radiation images from each of the radiation images is transferred after completion of the transfer of the plurality of thinned images.

24. A non-transitory computer-readable storage medium storing a computer program for causing a computer to execute a control method for a control apparatus, comprising:
wirelessly receiving in real time each of thinned images corresponding to a plurality of radiation images obtained by an imaging unit that is configured to obtain a plurality of radiation images as a moving image by performing imaging a plurality of times; and
displaying the plurality of thinned images as a moving image on a display device, wherein
in the receiving, each of remaining untransferred images obtained by excluding the each of thinned images corresponding to each of the radiation images from each of the radiation images is received after completion of the reception of the plurality of thinned images, and
in the displaying, after the reception of the untransferred images, the plurality of radiation images are displayed as a moving image on the display device.

* * * * *